(12) United States Patent
Vecchiotti et al.

(10) Patent No.: US 12,310,805 B2
(45) Date of Patent: May 27, 2025

(54) FLUSHING DEVICES AND METHODS

(71) Applicant: MOKITA MEDICAL GMBH, Berlin (DE)

(72) Inventors: Richard Gerard Vecchiotti, Berlin (DE); Tilo Kölbel, Hamburg (DE); Ernest G Schutt, San Diego, CA (US)

(73) Assignee: MOKITA MEDICAL GMBH, Berlin (DE)

( * ) Notice: Subject to any disclaimer, the term of this patent is extended or adjusted under 35 U.S.C. 154(b) by 609 days.

(21) Appl. No.: 17/639,112

(22) PCT Filed: Aug. 26, 2020

(86) PCT No.: PCT/EP2020/073860
§ 371 (c)(1),
(2) Date: Feb. 28, 2022

(87) PCT Pub. No.: WO2021/037917
PCT Pub. Date: Mar. 4, 2021

(65) Prior Publication Data
US 2022/0296336 A1 Sep. 22, 2022

Related U.S. Application Data

(60) Provisional application No. 62/961,952, filed on Jan. 16, 2020, provisional application No. 62/892,815, filed on Aug. 28, 2019.

(51) Int. Cl.
*A61B 90/70* (2016.01)
*A61M 39/00* (2006.01)
*A61M 39/22* (2006.01)

(52) U.S. Cl.
CPC ............ *A61B 90/70* (2016.02); *A61M 39/225* (2013.01); *A61B 2090/701* (2016.02); *A61M 2039/0018* (2013.01); *A61M 2202/02* (2013.01)

(58) Field of Classification Search
CPC ..... A61B 90/00; A61B 90/70; A61B 2090/00; A61B 2090/70; A61B 2090/701;
(Continued)

(56) References Cited

U.S. PATENT DOCUMENTS

| | | | |
|---|---|---|---|
| 5,224,933 A | 7/1993 | Bromander | |
| 8,118,042 B2 * | 2/2012 | Ngo | G01N 35/1004 |
| | | | 134/169 C |

(Continued)

FOREIGN PATENT DOCUMENTS

| | | |
|---|---|---|
| EP | 0711570 A1 | 5/1996 |
| EP | 2245468 B1 | 12/2012 |

OTHER PUBLICATIONS

International Search Report for PCT/EP2020/073860 Dated Nov. 13, 2020.

*Primary Examiner* — Natasha E Young
(74) *Attorney, Agent, or Firm* — Christopher M. Scherer; DeWitt LLP

(57) ABSTRACT

The present invention relates to a system for flushing a medical device, comprising a multi-port valve for controlling the delivery of flushing fluids, the multi-port valve connected to a source of pressurised flushing gas; a fluid outlet for coupling flushing fluids to the medical device; and, a gas-driven pump connected to the fluid outlet, wherein, in a first configuration, the multi-port valve couples a flow of gas from the source of pressurised flushing gas to the fluid outlet, and wherein, in a second configuration, the multi-port valve couples a flow of gas from the source of pressurised flushing gas to the gas-driven pump to drive the gas-driven pump thereby to provide a flow of flushing liquid to the fluid outlet.

20 Claims, 3 Drawing Sheets

(58) Field of Classification Search
CPC ................ A61M 5/0014; A61M 5/142; A61M 5/14212; A61M 5/145; A61M 5/155; A61M 5/30; A61M 5/36; A61M 39/00; A61M 39/22; A61M 39/223; A61M 39/224; A61M 39/225; A61M 2005/00; A61M 2005/14; A61M 2005/1401; A61M 2005/1402; A61M 2005/1403; A61M 2039/00; A61M 2039/0009; A61M 2039/0018; A61M 2202/00; A61M 2202/02

See application file for complete search history.

(56) References Cited

U.S. PATENT DOCUMENTS

| | | | |
|---|---|---|---|
| 8,124,028 B2* | 2/2012 | Fulton | .................... G01N 35/10 |
| | | | 422/50 |
| 2006/0258011 A1 | 11/2006 | Shvets et al. | |
| 2007/0181157 A1 | 8/2007 | Dadourian | |
| 2015/0051487 A1 | 2/2015 | Uber, III | |
| 2017/0025800 A1 | 1/2017 | Melino, Jr. | |
| 2017/0072592 A1 | 3/2017 | Amstutz | |
| 2017/0143446 A1 | 5/2017 | Kölbel | |
| 2017/0326541 A1 | 11/2017 | Virtanen et al. | |
| 2017/0367861 A1 | 12/2017 | Kölbel | |
| 2018/0168838 A1 | 6/2018 | Kratzberg | |

\* cited by examiner

FLUSHING DEVICES AND METHODS

CROSS-REFERENCE TO RELATED APPLICATIONS

The present application is the U.S. National Stage application of International Application No. PCT/EP2020/073860, filed Aug. 26, 2020, which International Application was published on Mar. 4, 2021, as International Publication No. WO2021/037917. The International Application claims priority to U.S. Provisional Patent Application No. 62/961,952, filed Jan. 16, 2020, and U.S. Provisional Patent Application No. 62/892,815, filed Aug. 28, 2019, the contents of which are incorporated herein by reference in their entireties.

BACKGROUND

Procedures that intervene with vasculature that is in communication with the cerebral vasculature can put patients at risk of cerebral injury if gaseous volumes enter the blood stream.

Flushing medical devices with a flushing fluid, such as medical grade saline, prior to an intravenous procedure to displace air from medical devices in order to reduce the risk of air entering the blood stream has become common practice.

It has more recently been proposed to flush medical devices with solutions such as degassed saline and perfluorocarbons. Flushing with these solutions has the effect of absorbing pockets of air that remain trapped when flushing with standard solutions such as saline.

SUMMARY OF THE INVENTION

According to an aspect of the invention, there is provided a system for flushing a medical device, comprising: a multi-port valve for controlling the delivery of flushing fluids, the multi-port valve connected to: a source of pressurised flushing gas; a fluid outlet for coupling flushing fluids to the medical device; and, a gas-driven pump connected to the fluid outlet, wherein, in a first configuration, the multi-port valve couples a flow of gas from the source of pressurised flushing gas to the fluid outlet, and wherein, in a second configuration, the multi-port valve couples a flow of gas from the source of pressurised flushing gas to the gas-driven pump to drive the gas-driven pump thereby providing a flow of flushing liquid to the fluid outlet.

Flushing medical devices with multiple flushing fluids, using existing devices, requires multiple sources of flushing fluids to be attached and detached for each medical device that is to be flushed, which can be time consuming. Each flush additionally requires the flushing fluid to be forced through the medical device which may require substantial operational force to generate sufficient pressure. While flushing gases can be compressed and stored at pressure, this is not possible for flushing liquids.

The system of the present invention simplifies the flushing process by allowing a medical device to be flushed using a single pressurised source to drive both a flushing gas and a flushing liquid. Flushing first with a flushing gas displaces ambient air in the medical device, and subsequently flushing with a flushing liquid displaces or dissolves the flushing gas. Multiple fluids are used to both displace and absorb the gases that make up ambient air contained within medical devices or any intermediate flushing fluid.

The term flushing fluid may refer to both a flushing liquid and a flushing gas.

The medical device could be a catheter or a device carried by a catheter, such as a stent graft or specialised tools housed within a catheter. The gas-driven pump may also be referred to as a pneumatic pump. The pump may be any gas-driven pump capable of pumping a flushing liquid, for example it may comprise a gas-driven piston or a gas-driven rotary mechanism such as a propeller or turbine.

Sterile filters can be placed in the fluid paths to ensure that the device maintains sterility.

The multi-port valve can be any valve capable of controllably directing an input flow of fluid between two or more output ports, e.g. a valve with one input port and two output ports, where the flow is controllably directed through only one of the output ports. For example, it could be a three-way valve, such as an L-port three way valve.

The flushing gas source could be a cartridge or canister of flushing gas, or it could be an external supply with a line-in connection.

The fluid outlet may be a valve.

The flushing fluid source could be a collapsible or vented container so that flushing liquid can be drawn from the source by the pump.

Preferably, in a third configuration, the multi-port valve couples the flow of gas from the source of pressurised flushing gas to the gas-driven pump to drive the gas-driven pump thereby to draw flushing liquid from a respective one of one or more sources of flushing liquid. The flushing liquid may optionally be drawn into a receptacle. The receptacle may be coupled to a piston of the gas-driven pump. Optionally, the gas-driven pump may comprise the receptacle. Flushing liquids may be sequentially drawn from the sources of flushing liquid and used to sequentially flush the medical device with different flushing liquids.

This allows for a single system that can flush a medical device with a flushing gas, draw a flushing liquid from a source, and flush the medical device with the flushing liquid. This simplifies and shortens the flushing process when flushing sequentially with multiple fluids.

Alternatively, the pump may be coupled to a pre-loaded receptacle of flushing fluid such that it is not necessary to draw flushing fluid.

Preferably, the system further comprises one or more additional valves for controlling the flow of gas from the source of pressurised flushing gas to the gas-driven pump.

Preferably, in the second configuration, the flow of gas from the source of pressurised flushing gas is coupled to a first chamber of the gas driven pump, and, in the third configuration, the flow of gas from the source of pressurised flushing gas is coupled to a second chamber of the gas driven pump.

This allows the flushing gas to drive the pump in opposite directions. The flow of flushing gas may be coupled to the pump in any way that allows the pump to be driven in opposite directions, with or without first and second chambers. For example, the flow of gas may drive a piston or turbine or similar rotary drive in opposite directions, which may be achieved by using valves to reverse the flow direction of the flushing gas within the pump.

Preferably, the system further comprises a pressure relief valve. This prevents excess pressure building in the system.

Preferably, the flushing gas is an acidic gas and the flushing fluid is a buffer solution comprising a buffering agent. Using a buffer solution increases the gas dissolving capacity of the flushing fluid, which leads to improved flushing. The flushing fluid may also be saline.

Preferably, the flushing gas is one selected from a group consisting of carbon dioxide, sulphur dioxide, and chlorine.

The buffering agent can be any biocompatible buffer than maintains a basic pH. Preferably the buffering agent is one or more selected from a group consisting of glycine, lysine, ammonium, borate, TRIS (tris(hydroxymethyl)aminomethane), HEPES (4-(2-hydroxyethyl)-1-piperazineethanesulfonic acid), phosphate, histidine, and arginine. More preferably, the buffering agent is selected from the group consisting of glycine, lysine and ammonium.

Optionally, the flushing fluid may be pH-adjusted. The pH of the buffer solution may be adjusted for example by using sodium hydroxide, NaOH, to increase the pH and hydrochloric acid, HCl, to lower the pH.

Preferably, the flushing fluid has a pH of 7 to 10.5, preferably 8 to 10, more preferably 8.5 to 10, even more preferably 9.5 to 9.7, and most preferably 9.6.

Preferably, a strength or concentration of the buffering agent in the buffer solution is 0.01 molar to 1.0 molar, preferably 0.05 molar to 0.5 molar, and most preferably 0.1 molar.

Alternatively, the flushing gas may be a basic gas, such as ammonia, formaldehyde, ethylene oxide, acetaldehyde or propionaldehyde, preferably ammonia. Ammonia is a basic gas that is absorbed by acidic buffers like phosphate and acetate at a preferable pH 5.

Alternatively, the flushing liquid may be an acidic buffer. Preferably, the acidic buffer comprises phosphate or acetate.

Optionally, the flushing liquid may be saline. Ammonia is very soluble in saline, so a saline flushing liquid will absorb an ammonia flushing gas.

Preferably, at least the multi-port valve is manually configurable or electronically configurable. Any or all of the valves may be manually or electronically configurable. Electronically configurable valves may be coupled to a console with an electronic controller. The console can be a part of a stand-alone system or be integrated into a separate entity.

Optionally, the system may further comprise one or more additional gas-driven pumps connected to the fluid outlet, wherein in a fourth configuration the multi-port valve selectively couples a flow of gas from the source of pressurised flushing gas to a respective one of the one or more additional gas-driven pumps to drive the respective one of the one or more additional gas-driven pumps thereby to provide a flow of flushing liquid to the fluid outlet.

According to another aspect of the invention, there is provided a method of flushing a medical device, comprising: flushing the medical device with a flow of flushing gas from a source of pressurised flushing gas; and/or, flushing the medical device with a flow of flushing liquid, wherein the flow of flushing liquid is provided by a gas-driven pump driven by a flow the flushing gas from the source of pressurised flushing gas.

Preferably, the flow of flushing gas is controlled by a multi-port valve. The multi-port valve can be any valve capable of controllably directing an input flow of fluid between two or more output ports, e.g. a valve with one input port and two output ports, where the flow is controllably directed through only one of the output ports. For example, it could be a three-way valve, such as an L-port three way valve.

Optionally, the method further comprises drawing flushing liquid from a respective one of one or more sources of flushing liquid, wherein the flushing liquid is drawn by the gas-driven pump driven by the flow of flushing gas from the source of pressurised flushing gas.

Optionally, the method further comprises, subsequent to flushing the medical device with the flow of flushing liquid, drawing another flushing liquid from a another respective one of the one or more sources of flushing liquid, wherein the other flushing liquid is drawn by the gas-driven pump driven by the flow of flushing gas from the source of pressurised flushing gas; and, flushing the medical device with a flow of the other flushing liquid, wherein the flow of the other flushing liquid is provided by a gas-driven pump driven by the flow of flushing gas from the source of pressurised flushing gas.

Preferably, the flushing gas is an acidic gas and the flushing fluid is a buffer solution comprising a buffering agent. Using a buffer solution may increase the gas dissolving capacity of the flushing fluid, which leads to improved flushing. The flushing fluid may also be saline.

Preferably, the flushing gas is one selected from a group consisting of carbon dioxide, sulphur dioxide, chlorine.

The buffering agent can be any biocompatible buffer than maintains a basic pH. Preferably, the buffering agent is one or more selected from a group consisting of glycine, lysine, ammonium, borate, TRIS (tris(hydroxymethyl)aminomethane), HEPES (4-(2-hydroxyethyl)-1-piperazineethanesulfonic acid), phosphate, histidine, and arginine. More preferably, the buffering agent is selected from the group consisting of glycine, lysine and ammonium.

Preferably, the flushing fluid is pH-adjusted. The pH of the buffer solution may be adjusted for example by using sodium hydroxide NaOH to increase the pH and hydrochloric acid HCl to lower the pH.

Preferably, the flushing fluid has a pH of 7 to 10.5, preferably 8 to 10, more preferably 8.5 to 10, even more preferably 9.5 to 9.7, and most preferably 9.6.

Preferably, a strength or concentration of the buffering agent in the buffer solution is 0.01 molar to 1.0 molar, preferably 0.05 molar to 0.5 molar, and most preferably 0.1 molar.

Alternatively, the flushing gas may be a basic gas, such as ammonia, formaldehyde, ethylene oxide, acetaldehyde or propionaldehyde, preferably ammonia. Ammonia is a basic gas that is absorbed by acidic buffers like phosphate and acetate at a preferable pH 5.

Alternatively, the flushing liquid may be an acidic buffer. Preferably, the acidic buffer comprises phosphate or acetate.

Optionally, the flushing liquid may be saline. Ammonia is very soluble in saline, so a saline flushing liquid will absorb an ammonia flushing gas.

Optionally, the method further comprises flushing the medical device with a flow of a respective one of one or more additional flushing liquids, wherein the flow of the respective one of one or more additional flushing liquids is provided by a respective one of one or more additional gas-driven pumps driven by a flow of flushing gas from the source of pressurised flushing gas.

According to another aspect of the invention, there is provided a method of flushing a medical device, comprising flushing the medical device with a first flushing fluid; and subsequent to flushing the medical device with the first flushing fluid, flushing the medical device with a second flushing fluid, wherein the second flushing fluid is a first buffer solution. In an alternative aspect the second flushing fluid is saline.

Using a buffer solution as the second flushing fluid augments the second flushing fluid's ability to dissolve the flushing gas and greatly increases the gas dissolving capacity of the flushing fluid, which leads to improved flushing due to more effective removal of gas from the medical device. Therefore it is highly preferred that the first flushing fluid is a gas.

In an embodiment, the method further comprises flushing the medical device with a third, fourth or nth flushing fluid before or after flushing the medical device with the second flushing fluid, wherein the third flushing fluid is a second buffer solution or saline. The third flushing fluid may be any of the buffer solutions described elsewhere in this specification in the context of the second flushing fluid.

In a highly preferred embodiment of any aspect described above, before the step of flushing the medical device with the second flushing fluid, the method comprises the step of flushing the medical device with at least one intermediate flushing fluid to mechanically displace the first flushing fluid. Thereafter, the medical device is flushed with the second flushing fluid and optionally third flushing fluid. In this embodiment, it is preferred that the first flushing fluid is a gas.

Preferred combinations of first and intermediate flushing fluids include, but are not limited to: carbon dioxide and aqueous sodium bicarbonate solution; carbon dioxide and a buffer having a pH of from 2 to 6, preferably of from 4 to 5, such as acetate buffer; and carbon dioxide and saline having a pH of from 2 to 6, preferably of from 4 to 5; and ammonia, formaldehyde, ethylene oxide, acetaldehyde or propionaldehyde and a basic buffer as described in this specification.

Preferably the first flushing fluid is carbon dioxide and the intermediate flushing fluid is aqueous sodium bicarbonate solution. Preferably the concentration of the aqueous sodium bicarbonate solution is from 1 to 0.01 molar, more preferably from 0.1 to 0.2 molar.

Preferably the first flushing fluid is carbon dioxide, the second flushing fluid, and optionally third flushing fluid, is a basic buffer selected from glycine, lysine and ammonium and the intermediate flushing fluid is aqueous sodium bicarbonate solution.

In an embodiment the method further comprises the step of flushing the medical device with saline after flushing the medical device with the second flushing fluid and optionally third flushing fluid. In a preferred embodiment the step of flushing the medical device with saline is the last flushing step in the flushing sequence.

In the alternative aspect of the method, preferably the first flushing fluid is carbon dioxide, the second flushing fluid is saline, optionally the third flushing fluid is saline and the intermediate flushing fluid is aqueous sodium bicarbonate solution.

In another highly preferred embodiment of any aspect described above the first flushing fluid is a gas and the intermediate flushing fluid comprises a viscosity increasing agent.

In another highly preferred embodiment of any aspect described above the first flushing fluid is a gas and the intermediate flushing fluid comprises a density increasing agent.

In another preferred embodiment, the intermediate flushing fluid comprises a viscosity increasing agent and a density increasing agent.

In an embodiment, the intermediate flushing fluid comprises a density increasing agent and the method further comprises flushing the medical device with a further intermediate flushing fluid comprising a viscosity increasing agent before or after flushing the medical device with the intermediate flushing fluid comprising a density increasing agent.

In an embodiment, the intermediate flushing fluid comprises a viscosity increasing agent and the method further comprises flushing the medical device with a further intermediate flushing fluid comprising a density increasing agent before or after flushing the medical device with the intermediate flushing fluid comprising a viscosity increasing agent.

In an embodiment, the intermediate flushing fluid comprises a density increasing agent and the method further comprises flushing the medical device with a further intermediate flushing fluid before or after flushing the medical device with the intermediate flushing fluid comprising a density increasing agent.

In an embodiment, the intermediate flushing fluid comprises a viscosity increasing agent and the method further comprises flushing the medical device with a further intermediate flushing fluid before or after flushing the medical device with the intermediate flushing fluid comprising a viscosity increasing agent.

Preferably the viscosity increasing agent is selected from hydroxyethyl starch, gelatin and dextran, and combinations thereof. Preferably the viscosity increasing agent is included in a sufficient amount to increase the viscosity of the second and/or third flushing fluid by a factor of 1.5 to 100, preferably 5 to 10.

Preferably the density increasing agent is sodium chloride. Preferably the density increasing agent is incorporated in the second and/or third flushing fluid to increase the density of the second and/or third flushing fluid by a factor of 1.05 to 2.5, preferably 1.1 to 1.2.

The first and/or second buffering agent can be any biocompatible buffer than maintains a basic pH. Preferably, the second and/or third flushing fluid comprises a buffering agent that is one or more selected from the group consisting of glycine, lysine, ammonium, borate, TRIS (tris(hydroxymethyl)aminomethane), HEPES (4-(2-hydroxyethyl)-1-piperazineethanesulfonic acid), phosphate, histidine, and arginine. More preferably, the buffering agent is selected from the group consisting of glycine, lysine and ammonium.

Preferably, the second and/or third flushing fluid is pH-adjusted. The pH of the first and/or second buffer solution may be adjusted for example by using sodium hydroxide NaOH to increase the pH and hydrochloric acid HCl to lower the pH.

Preferably, the second and/or third flushing fluid has a pH of 7 to 10.5, preferably 8 to 10, more preferably 8.5 to 10, even more preferably 9.5 to 9.7, and most preferably 9.6.

Preferably, a strength or concentration of the buffering agent in the first and/or second buffer solution is 0.01 molar to 1.0 molar, preferably 0.05 molar to 0.5 molar, and most preferably 0.1 molar.

Preferably, the first flushing fluid is an acidic gas.

Preferably, the first flushing fluid is one selected from a group consisting of carbon dioxide, sulphur dioxide, and chlorine.

Alternatively, the first flushing fluid may be a basic gas, such as ammonia, formaldehyde, ethylene oxide, acetaldehyde or propionaldehyde, preferably ammonia. Ammonia is a basic gas that is absorbed by acidic buffers like phosphate and acetate at a preferable pH 5.

Optionally, the second and/or third flushing fluid may be saline. Ammonia is very soluble in saline, so a saline flushing liquid will absorb an ammonia flushing gas.

Alternatively, the second and/or third flushing fluid may be an acidic buffer. Preferably, the acidic buffer comprises phosphate or acetate.

According to another aspect, there is provided a method of flushing a medical device, comprising: flushing the medical device with a flow of flushing liquid, wherein the flow of flushing liquid is provided by a gas-driven pump driven by a flow of gas from a source of pressurised gas.

According to another aspect, there is provided a kit comprising a medical device and instructions for use for the medical device, wherein the instructions for use comprise a description of a method as defined herein.

Preferably, the medical device is an intravenous catheter.

Preferably, the kit further comprises a system as defined herein and/or one or both of a flushing gas and a flushing liquid. More preferably, the flushing gas and/or the flushing liquid are as described herein.

BRIEF DESCRIPTION OF DRAWINGS

Examples of the present invention will now be described in detail with reference to the accompanying drawings, in which.

DETAILED DESCRIPTION

The present invention provides an improved flushing system and methods for sequentially flushing medical devices with multiple flushing fluids.

Figure 1:
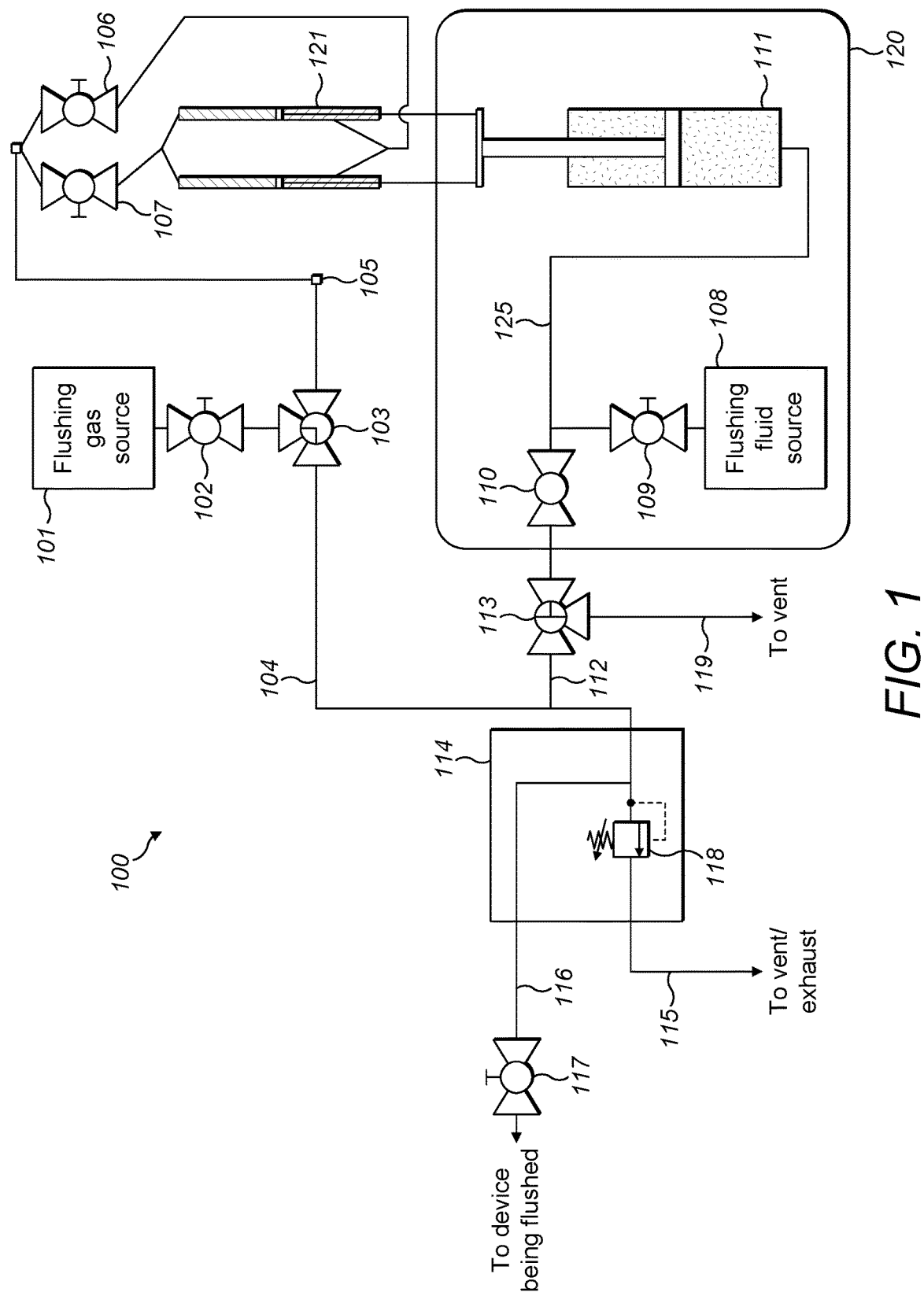
FIG. 1 shows a system for flushing a medical device.

An example flushing system 100 is shown in FIG. 1. The system 100 comprises a flushing gas source 101 and a flushing fluid source 108.

The flushing gas may be any gas suitable for displacing ambient air from a medical device, for example it could be one or a combination of carbon dioxide, ammonia, sulphur dioxide, and chlorine. The flushing gas source 101 may be a cartridge or canister of flushing gas, or it may be an external supply with a line-in connection. A sterile filter (not shown) may optionally be used to filter the flushing gas to prevent microbe contamination.

The flushing fluid will generally be a liquid and can be any fluid capable of displacing, and preferably dissolving, the flushing gas. The flushing fluid may also be used to neutralise the flushing gas. Examples of flushing fluids include medical grade saline, perfluorocarbon liquids and perfluorocarbon emulsion liquids, and aqueous solutions of glycine, lysine, ammonium, borate, TRIS (tris(hydroxymethyl)aminomethane), HEPES (4-(2-hydroxyethyl)-1-piperazineethanesulfonic acid), phosphate, histidine, and arginine. Any flushing fluid may optionally be degassed using known techniques, such as vacuum treatment or sparging with helium. The flushing fluid source 108 may be a cartridge or canister, or it may be an external supply with a line-in connection. A sterile filter (not shown) may optionally be used to filter the flushing fluid to prevent microbe contamination.

The flushing gas source 101 is coupled to a main three-way valve 103 via a manually operated flushing gas source valve 102. The main valve 103 is a three-way L-port valve and allows the flow of flushing gas from the flushing gas source 101 to be directed either towards a manually operated main flush valve 117 via a central gas supply line 104, or towards a pair of manually operated actuator valves 106 and 107 via a pneumatic power supply line 105. The flushing gas source valve 102 controls the flow of the flushing gas.

The central gas supply line 104 is connected to a central valve construct 114 comprising a pressure relief valve 118 and a main flush line 116. The pressure relief valve 118 allows the flushing gas to be vented along a waste/exhaust line 115 in the event of excess system pressure. The main flush line 116 connects to the main flush valve 117, which acts as a fluid outlet for coupling to a medical device (not pictured) for flushing.

Figure 2A:
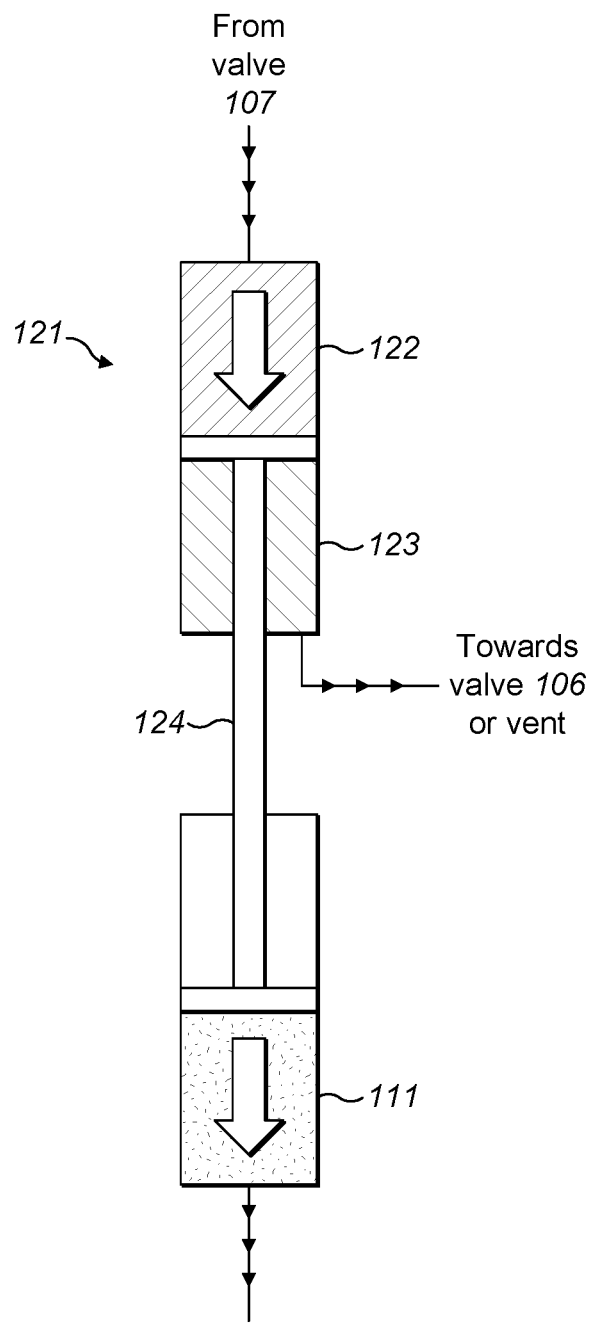
FIGS. 2A and 2B show the operation of a gas-driven pump for use in the system of FIG. 1.
Figure 2B:
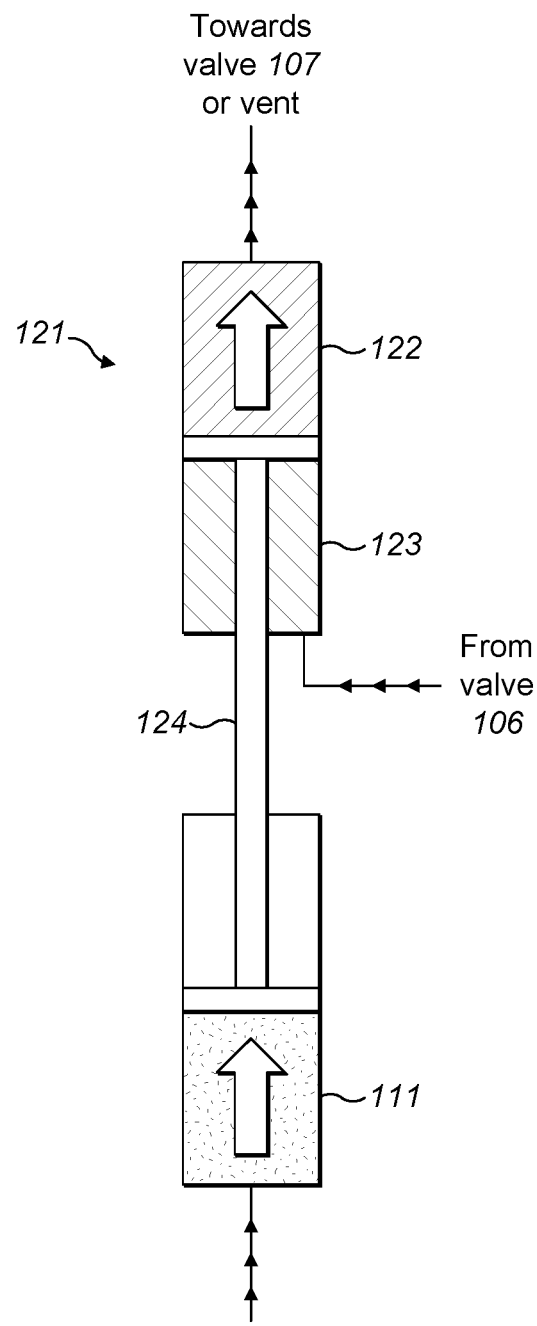

When the flushing gas source 101 is directed along the pneumatic power supply line 105 by main valve 103, the actuator valves 106 and 107 are used to control a gas-driven or pneumatic pump 121, as illustrated in FIGS. 2A and 2B. The pump 121 illustrated in FIGS. 2A and 2B comprises variable upper and lower chambers 122 and 123 respectively defined by a moveable piston 124. The piston 124 is coupled to a receptacle 111, which may optionally be adjustable to set volumes for flushing specific medical devices, i.e. it may have adjustable hard stops. Unlike the pump in FIGS. 2A and 2B, the pump illustrated in FIG. 1 comprises multiple pump cylinders, each with upper and lower chambers coupled to separate piston shafts.

It will be understood that the particular arrangement of the pump, including the number of cylinders and the size of the chambers, can be adjusted as needed. In particular, the dimensions of the pump can be chosen according to gas and pressure laws to ensure that the pump operates appropriately for flushing medical devices. For example, the driving force of the pump can be altered by changing the pressure of the flushing gas source or the surface area ratio of the flushing solution piston to the pneumatic piston or pistons area.

It will also be understood that a different form of gas-driven pump may be used that does not drive a piston, for example a rotary pump with a turbine or propeller. Alternatively, the pump 121 may couple to a pre-loaded receptacle of flushing fluid such that a separate flushing fluid source 108 is not needed.

Opening actuator valve 107 and closing actuator valve 106 allows the flushing gas to flow into the upper chamber 122, as illustrated in FIG. 2A. The flow of flushing gas into the upper chamber 122 creates a pressure gradient between the upper chamber 122 and the lower chamber 123, which causes the upper chamber 122 to expand and drives the piston 124 to force flushing liquid out of the pump 121. Fluid in the lower chamber 123 is either compressed or optionally vented through one or more valves (not pictured).

Similarly, opening the actuator valve 106 and closing the actuator valve 107 allows the flushing gas to flow into the lower chamber 123, as illustrated in FIG. 2B. This creates a pressure gradient between the lower chamber 123 and the upper chamber 122, which causes the lower chamber 123 to expand and drives the piston 124 into the pump. Fluid in the upper chamber 122 is either compressed or vented through one or more valves (not pictured).

The receptacle 111 is coupled to the flushing fluid source 108 using supply line 125 via a manually operated flushing fluid source valve 109. It is also coupled to the central valve construct 114 via a flushing fluid flush valve 110 and a three-way T-port fluid inlet valve 113, which is in turn coupled to a vent line 119.

The flushing fluid source 108, flushing fluid source valve 109, flushing fluid flush valve 110 and receptacle 111 are collectively referred to as a fluid unit 120.

In a first configuration of the system 100, flushing gas from the flushing gas source 101 is used to flush a medical device. In this configuration, the main valve 103 is configured to direct flushing gas along the central gas supply line 104, and the fluid inlet valve 113 is configured to prevent flushing gas flowing towards flushing fluid flush valve 110. Although the configuration of valves 106, 107, 109 and 110 does not matter for the first configuration, valves 109 and 110 are ideally closed. A user can then use the system 100 to flush a medical device by coupling the medical device to main flush valve 117 and opening valves 102 and 117.

In a second configuration of the system 100, flushing gas from the flushing gas source 101 is used to drive the pump 121 to draw flushing fluid from the flushing fluid source 108. In this configuration, the main valve 103 is configured to direct flushing gas along the pneumatic power supply line 105, while valves 107 and 110 are closed. Although the configuration of valves 113 and 117 does not matter for the second configuration, valve 117 is ideally closed. The user can then draw flushing fluid from the flushing fluid source 108 by opening valves 102, 106 and 109. This will cause a pressure gradient between the lower and upper chambers 123 and 122, as described above, which will in turn retract piston 124 and expand the flushing fluid volume within receptacle 111, thereby drawing flushing fluid from the flushing fluid source 108. The flushing fluid source 108 is ideally a collapsible or vented container so that flushing liquid can be drawn from the source by the pump.

In a third configuration of the system 100, the flushing gas source 101 is used to drive the pump 121 to provide a flow of flushing fluid to flush a medical device. In this configuration, the main valve 103 is configured to direct flushing gas along the pneumatic power supply line 105, valve 110 is open, valve 113 is configured in an open configuration to allow fluid to flow from the fluid unit 120 towards the main flush line 116 but not to the vent line 119, and valves 106 and 109 are closed.

The user can then operate the system 100 to provide a flow of flushing fluid to flush a medical device by opening valves 102, 107 and 117. This will cause a pressure gradient between the upper and lower chambers 122 and 123, as described above, which will in turn drive piston 124 and exert a compressive force on the flushing fluid within receptacle 111, thereby forcing flushing fluid from the receptacle 111.

Unless indicated otherwise, the various components of FIG. 1, such as the valves, pump and sources, are coupled by supply lines that may be any type of medical-grade tubing suitable for permitting a flow of flushing fluids for flushing medical devices at the required flushing pressure. Reference to coupling should therefore be understood to include coupling by means of such supply lines. The supply lines and vent lines are preferably compatible with disposal containers.

Figure 3:
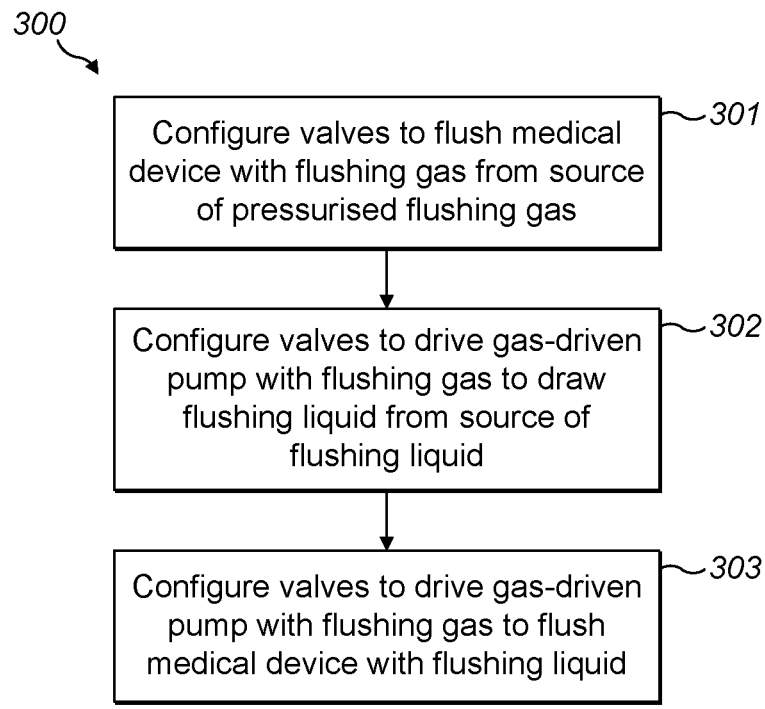
FIG. 3 is a method for flushing a medical device.

In addition to the above configurations, the system 100 also allows for flushing of the supply lines to prepare the system 100 for flushing. An exemplary flushing method 300, including optional preparation steps, will now be described in relation to FIG. 3.

In the initial configuration of the system 100, valves 102, 109, 110 and 117 are off/closed, and fluid inlet valve 113 is closed to the central fluid supply line 112. The flushing gas source 101 is coupled to the flushing gas valve 102.

The system 100 is then prepared for a new cycle. The main flush valve 117 is opened, and the pressure relief valve 118 is opened to permit the flow of fluid at all pressures. The flushing gas valve 102 is opened and the main valve 103 is configured to couple the flow of flushing gas from the flushing gas source 101 to the central gas supply line 104. This flushes the supply lines 104, 115 and 116 with flushing gas.

With the flushing gas still flowing, the main flush valve 117 is then closed, the pressure relief valve 118 is closed (i.e. to only allow the flow of over-pressure fluid), and the fluid inlet valve 113 is configured to couple the supply line 112 to the vent line 119. This flushes the supply line 112 with flushing gas. The flushing gas valve 102 is then closed and the fluid inlet valve 113 is configured to prevent flushing gas from flowing towards flushing fluid flush valve 110. Following these preparation steps, the system 100 will now be in primed state with all valves free of air.

The valves are then controlled to flush a medical device with the flushing gas in step 301. The medical device is first coupled to the main flush valve 117, and then valves 102 and 117 are opened to allow the flushing gas to flow from the flushing gas source 101 to the medical device. Flushing gas will automatically bleed out via the pressure relief valve 118 in the event of excess pressure. Once the medical device has been sufficiently flushed with the flushing gas, the main flush valve 117 and the flushing gas valve 102 are closed.

At step 302, the valves are controlled to draw flushing fluid from the flushing fluid source 108 into the receptacle 111. Valves 110 and 107 are closed, and main valve 103 is configured to direct flushing gas from the flushing gas source 101 along supply line 105 towards the pump 121. Actuator valve 106, flushing gas valve 102, and valve 109 are opened, which drives the pump 121 and causes flushing fluid to be drawn into the receptacle 111 from the flushing fluid source 108.

If necessary, the supply lines of the fluid unit 120 can be flushed with flushing fluid by closing valves 109 and 106 and opening valves 107 and 110 with valve 113 configured to couple the fluid unit 120 to the vent line 119 (but not supply line 112). The receptacle 111 can be topped up with flushing fluid if necessary following supply line flushing by repeating the procedure above.

The method then proceeds to step 303, at which point the medical device is flushed with the flushing fluid from the flushing fluid source 108 that has been drawn into the receptacle 111. The system 100 is configured with valves 102, 107, 110, and 117 open, valves 106 and 109 closed, valve 113 coupling the fluid unit 120 to the central fluid supply line 112 (but not vent line 119); and main valve 103 coupling the flushing gas from the flushing gas source 101 along supply line 105 towards the pump 121. The flushing gas from the flushing gas source 101 drives the pump 121 to provide a flow of flushing fluid to the fluid outlet 117.

Once the medical device is sufficiently flushed, valves 117, 110 and 102 are closed and the medical device is disconnected from the valve 117.

The above method steps could alternatively be performed in a different order, for example the fluid drawing step 302 could be performed prior to flushing the medical device with the flushing gas. It is also envisaged that the gas-driven pump 121 could couple to a pre-loaded receptacle of flushing fluid such that step 302 need not be performed at all.

Alternative embodiments of the system 100 are envisaged in which additional flushing fluid sources are used. Such systems may include additional gas-driven pumps 121, or may alternatively use a single gas-driven pump 121 and use additional valves to control the filling and flushing of flushing fluids from different flushing fluid sources coupled to supply line 125.

Multiple flushing fluid sources can be swapped in/out as component 108. Alternatively, multiple flushing fluid sources can be attached (via separate controlling valves) to supply line 125.

The valves in the system, including those referred to as manually operated, may be individually controlled by the user, or multiple valves may be controlled by a single actuator that configures the system 100 for system preparation and each stage of the flushing method 300. For example, the actuator may be a labelled mechanical rotary knob, possibly mounted to a crankshaft.

Alternatively, all or some of the valves, including those referred to as manually operated, may be controlled electronically and be coupled to a console with an electronic controller.

Alternative embodiments are also envisaged with different valve and pump arrangements being used to achieve the same purpose. For example, the actuator valves 106 and 107 could be replaced with a single three-way valve for controlling the flow of flushing gas to the pump 121. The arrangement given in FIG. 1 is one exemplary embodiment of how the system 100 could be arranged.

The pump 121 could be replaced by a rigid container containing a soft pouch of flushing fluid, with the flushing gas source connected to the rigid container by one or more supply lines and used to provide pressure to drive the flushing fluid out of the pouch and container. In this case the container may be pre-loaded with the pouch of flushing fluid such that there is no need to draw flushing fluid from a flushing fluid source.

The ideal end result at the conclusion of the flushing process is to have a medical device that is free from ambient air and filled with a liquid that is safe for vascular communication. It is envisaged that the medical device may be further flushed with saline to displace and replace the flushing fluid. This could be performed by connecting a source of saline to the system 100 and flushing using a similar procedure to that described above when flushing the medical device with the flushing liquid.

If any intermediate flushing agents are not completely removed, then it is advantageous for any residual flushing agents to be of a type that can safely be introduced into communication with the other flushing agents used in the flushing procedure and, in residual amounts, be introduced into communication with a patient's blood stream.

Figure 4:
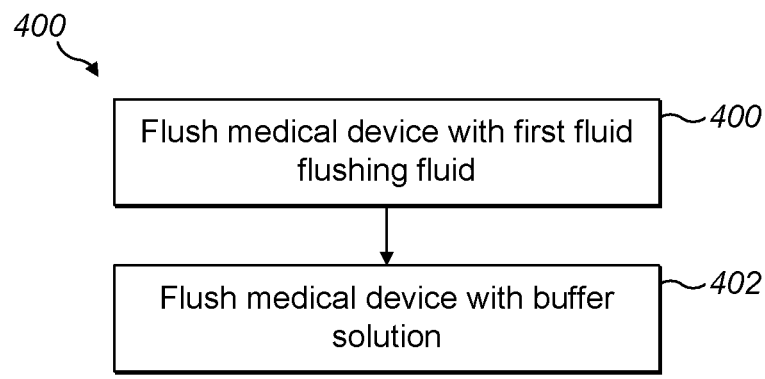
FIG. 4 is another method for flushing a medical device.

Flushing gases such as carbon dioxide, sulphur dioxide and chlorine are acidic. FIG. 4 illustrates a method 400 for flushing with an acidic gas followed by a buffer solution.

In step 401, the medical device is flushed with a first flushing fluid, which may be one of the acidic flushing gases listed above for example.

Subsequent to flushing the medical device with the first flushing fluid, the medical device is flushed in step 402 with a second flushing fluid, and optionally third flushing fluid, that is a buffer solution. For example, this second and/or third flushing fluid may be a buffer solution of saline or perfluorocarbon or emulsion and one or more of glycine, lysine, ammonium, borate, TRIS (tris(hydroxymethyl)aminomethane), HEPES (4-(2-hydroxyethyl)-1-piperazineethanesulfonic acid), phosphate, histidine or arginine. The solution may additionally be pH-adjusted to a desired pH value, for example by using sodium hydroxide NaOH to increase the pH and hydrochloric acid HCl to lower the pH.

When acidic flushing gases such as such as carbon dioxide, sulphur dioxide and chlorine dissolve in water, they can react with hydroxide ($OH^-$) ions to form a very water-soluble charged species in an equilibrium reaction. The high concentration of $OH^-$ ions present in a basic buffered aqueous solution pushes the equilibrium towards the water-soluble charged species, thereby greatly increasing the gas dissolving capacity of the solution. Similarly, when basic flushing gases, such as ammonia, dissolve in water, they react with hydrogen ions ($H^+$) to form a very water-soluble charged species in an equilibrium reaction. The high concentration of $H^+$ ions present in an acidic buffered aqueous solution pushes the equilibrium towards the water-soluble charged species, thereby greatly increasing the gas dissolving capacity of the solution.

The pH of the buffer solution should ideally be in the range pH 7 to 10.5 to ensure the acidic gas species equilibrium is pushed far toward the soluble charged species but not so basic that damage to medical devices could occur. The strength of the buffer is preferably 0.01 molar to 1.0 molar.

The pH-adjustment/basic buffer works by inhibiting the formation of carbonic acid $H_2CO_3$ at the interface of $CO_2$ and saline. When carbonic acid is formed at the interface of $CO_2$ and saline, this has an inhibitory effect on the saline's ability to dissolve additional $CO_2$. If the pH of saline can be adjusted to become basic, the $CO_2$ dissolved at the interface of the $CO_2$ and the saline can be forced into the creation of sodium carbonate $Na_2CO_3$, the water-soluble sodium salt of carbonic acid, rather than carbonic acid. The formation of sodium carbonate instead of carbonic acid will not saturate the $CO_2$/saline interface, thus allowing the saline to more fully dissolve any $CO_2$ it is exposed to.

Of the buffers listed above, a flushing gas of $CO_2$ used with a flushing gas dissolving buffer of lysine or glycine at pH 9.6 is particularly effective. $CO_2$ is biocompatible in the bloodstream and can easily and safely be handled in a clinical setting. Lysine and glycine are both amino acids present in the body and are biocompatible in the blood and also possess pKa values that make them good buffers at pH 9.6. The amino acid salts formed when dissolving carbon dioxide are also biocompatible. Both the gas and these buffers are also compatible with medical devices such as catheters.

Any of the buffers may optionally be used in a degassed or partially degassed state.

Before the step 402, the method may comprise the step of flushing the medical device with at least one intermediate flushing fluid to mechanically displace the first flushing fluid (not shown). Thereafter, the medical device is flushed with the second flushing fluid, and optionally third flushing fluid, in step 402. It will be appreciated by a skilled person that the intermediate flushing fluid mechanically displaces the first flushing fluid, whereas the second flushing fluid, and optionally the third flushing fluid, will both dissolve and mechanically displace any remaining first flushing fluid. A skilled person will appreciate that the intermediate flushing fluid does not dissolve much, if any, of the first flushing fluid. For example, when the first flushing fluid is a gas, the solubility of the first flushing fluid in the intermediate flushing fluid may be a mole fraction solubility of less than $10^{-5}$, preferably less than $10^{-6}$ at 25° C. and a partial pressure of 101.325 kPa (1 atm). A skilled person will be able to choose an appropriate intermediate flushing fluid based on the chosen first flushing fluid or vice versa. In this embodiment, it is preferred that the first flushing fluid is a gas. It is also preferred that the intermediate flushing fluid is a liquid.

As discussed, using a buffer solution augments the ability of the second flushing fluid, and optionally the third flushing fluid, to dissolve the first flushing fluid. The inventors have found that in certain instances, dissolution of the first flushing fluid in the second flushing fluid results in a pressure difference between environmental gas, such as air, and the first flushing fluid near to the second flushing fluid, which causes environmental gas to be drawn towards the medical device. It will be appreciated by a skilled person that this is particularly dangerous when, for example, the medical device comprises a lumen, such as a catheter, because environmental gas will be drawn into the lumen of the medical device and possibly become trapped. This is particularly dangerous in medical environments where environmental gas may not be sterile. The inventors have found that in such circumstances it is advantageous to flush the medical device with the intermediate flushing fluid to mechanically displace the first flushing fluid while not causing environmental gas to be drawn into the medical device. The second and optionally third flushing fluid is then used to absorb the residual, trace, amounts of the remaining first flushing fluid that has not been mechanically displaced.

Suitable combinations of first and intermediate flushing fluids include, but are not limited to: an acidic gas, such as carbon dioxide, sulphur dioxide or chlorine, and an acidic buffer, such as aqueous sodium bicarbonate solution; and a basic gas, such as ammonia, and a basic buffer, such as tris(hydroxymethyl)aminomethane buffer.

Preferably the first flushing fluid is carbon dioxide and the intermediate flushing fluid is aqueous sodium bicarbonate solution. If any carbon dioxide dissolves in the aqueous sodium bicarbonate solution, then acid formed by the dissolved carbon dioxide, such as carbonic acid, is neutralised in sodium bicarbonate solution, thereby evolving carbon dioxide, reducing any net change in volume of carbon dioxide. Therefore it is particularly advantageous to use this combination in order to further reduce the risk of drawing environmental gas towards the medical device.

Suitable combinations of first, second, optionally third, and intermediate flushing fluids include, but are not limited to: an acidic gas, such as carbon dioxide, sulphur dioxide or chlorine, as the first flushing fluid, a basic buffer, such as glycine, lysine, ammonium, borate, TRIS (tris(hydroxymethyl)aminomethane) HEPES (4-(2-hydroxyethyl)-1-piperazineethanesulfonic acid), phosphate, histidine, or arginine buffer; or saline as the second flushing fluid, and optionally the third flushing fluid, and an acidic buffer, such as aqueous sodium bicarbonate solution, as the intermediate flushing fluid.

According to an aspect of the invention, there is provided a method of flushing a medical device, comprising flushing the medical device with a first flushing fluid; flushing the medical device with at least one intermediate flushing fluid to mechanically displace the first flushing fluid; and flushing the medical device with a second flushing fluid, wherein the second flushing fluid is saline. In this aspect, it is preferred that the first flushing fluid is a gas. Suitable first and intermediate flushing fluids are described above. As described before, flushing the medical device with the intermediate flushing fluid to mechanically displace the first flushing fluid addresses the problem of drawing environmental gas towards the medical device.

In any of the above aspects the first flushing fluid may be a gas and the intermediate flushing fluid may comprise a viscosity increasing agent. By "viscosity increasing agent" is meant a substance which can increase the viscosity of the intermediate flushing fluid at a given temperature and pressure. As used herein, viscosity is measured using a Brookfield viscometer at 20±1° C. and at a shear rate of $10000s^{-1}$. It will be appreciated by a skilled person that the viscosity increasing agent should preferably be biocompatible. Suitable examples of viscosity increasing agent include, but are not limited to: hydroxyethyl starch, gelatin and dextran, and combinations thereof. The inventors have found that it is advantageous to include a viscosity increasing agent in the intermediate flushing fluid because this enhances the ability of the intermediate flushing fluid to mechanically displace the first flushing fluid without dissolving much, if any, of the first flushing fluid.

In any of the above aspects the first flushing fluid may be a gas and the intermediate flushing fluid may comprise a density increasing agent. By "density increasing agent" is meant an agent that can increase the density of the intermediate flushing fluid at a given temperature and pressure. As used herein, density is measured using a density meter, such as a Mettler Toledo Density meter Easy D30, at 20±1° C. Suitable examples of density increasing agents include, but are not limited to: salts, such as sodium chloride, monosodium phosphate, disodium phosphate, trisodium phosphate, sodium carbonate, sodium bromide, caesium bromide, lithium chloride and potassium iodide; amino acids such as lysine, and glycine; carbohydrates such as mannitol, glucose, sucrose and dextran; and organic compounds such as urea and propylene glycol; and combinations thereof. Similar to viscosity increasing agents, the inventors have found that it is advantageous to include a density increasing agent in the second and/or third flushing fluid because this increases the rate at which the first flushing fluid is dissolved and can increase the volume of gas dissolved by the second and/or third flushing fluid. Therefore, in a preferred embodiment the second and/or third flushing fluid comprises a viscosity increasing agent and a density increasing agent.

In an exemplary method according to the invention, the intermediate flushing fluid comprises a viscosity increasing agent, and the method further comprises flushing the medical device with a further flushing fluid comprising a density increasing agent before or after flushing the medical device with the intermediate flushing fluid.

In another exemplary method according to the invention, the intermediate flushing fluid comprises a density increasing agent, and the method further comprises flushing the medical device with a further flushing fluid comprising a viscosity increasing agent before or after flushing the medical device with the intermediate flushing fluid.

In another exemplary method according to the invention, the intermediate flushing fluid comprises a density increasing agent and the method further comprises flushing the medical device with a further intermediate flushing fluid before or after flushing the medical device with the intermediate flushing fluid comprising a density increasing agent.

In another exemplary method according to the invention, the intermediate flushing fluid comprises a viscosity increasing agent and the method further comprises flushing the medical device with a further intermediate flushing fluid before or after flushing the medical device with the intermediate flushing fluid comprising a viscosity increasing agent.

Method 400 could be used in combination with system 100 and/or method 300, or as a separate flushing method. The buffers may be prepared with the flushing liquid prior to connection to the system, or they may alternatively be added via subsequent connections to the supply line 125, in which case the pump 121 can be used to draw the buffer solution as required in the same manner that the flushing liquid is drawn from the flushing fluid source 108.

According to certain aspects of the invention, kits are provided. These kits contain a medical device and instructions for use for the medical device.

It is required by regulatory bodies such as the Food and Drug Administration (FDA) and the European Medicines Agency (EMA) that regulated medical devices are provided with instructions for use.

As a general principle, each device must be accompanied by as much information as is necessary for an operator to use it safely, taking into account the training and knowledge of the potential users. Certain basic instructions must appear on the label with more detailed copy to be included in the enclosed instructions for use (IFU).

The IFU must contain several particulars, including the details required on the label, any side effects from use of the device, and, as a general rule, details for its correct use, including any specific precautions.

For certain medical devices such as intravenous catheters, cleaning and sterilising instructions are very important, because they potentially affect the safety of using the device. Without proper cleaning, an instrument cannot be sterilised or disinfected. Cleaning procedures vary depending on the complexity of the device, so IFUs should always provide instructions on how to achieve thorough cleaning.

Some instruments have areas that are difficult to clean and may need to be disassembled. In these cases, the IFUs typically include diagrams for adequate disassembly and reassembly. Cleaning chemistries are also included since not only can the materials be harmed if the wrong type of cleaning solution is used, but many are only effectively cleaned when using the correct ratio of cleaning chemicals to water, for example.

Medical devices with channels, such intravenous catheters, require channel flushing to clean. Proper channel flushing is important to remove gasses (e.g. air) from inside these devices, as described above. IFUs provide flushing instructions along with information about the specific accessories to be used, including the flushing agent. The kits containing the medical devices and the IFU may also contain these accessories, such as flushing agents or flushing apparatus. According to the present invention, the kits may comprise these accessories together with the medical device.

According to the present invention, the descriptions of the methods as defined herein are preferably included within the 'cleaning' section of the IFU.

The IFU may therefore be a critical component of the kits according to the invention. They are a technical part of the invention because following the IFU is required by regulatory bodies. The device cannot be provided or used without following the guidelines in the IFU.

As used herein, unless specifically mentioned otherwise, any reference to the state of matter such as gas or liquid means the state of matter at 25° C. and 1 atm.

It will be understood that the above systems and methods and accompanying figures are non-limiting examples, and other configurations are possible to carry out the invention.

The invention claimed is:

1. A method of flushing a medical device, comprising:
   flushing the medical device with a first flushing fluid; and
   subsequent to flushing the medical device with the first flushing fluid, flushing the medical device with a second flushing fluid,
   wherein the first flushing fluid is carbon dioxide and the second flushing fluid is a first buffer solution.

2. The method of claim 1, further comprising flushing the medical device with at least one intermediate flushing fluid, prior to flushing the medical device with a second flushing fluid, to mechanically displace the first flushing fluid.

3. The method of claim 2, wherein the intermediate flushing fluid is aqueous sodium bicarbonate solution.

4. The method of claim 1, wherein the intermediate flushing fluid comprises a viscosity increasing agent.

5. The method of claim 1, wherein the intermediate flushing fluid comprises a density increasing agent.

6. The method of claim 4, further comprising flushing the medical device with a further intermediate flushing fluid before or after flushing the medical device with the intermediate flushing fluid comprising a viscosity increasing agent and/or a density increasing agent.

7. The method of claim 4, further comprising flushing the medical device with an intermediate flushing fluid comprising a density increasing agent before or after flushing the medical device with the intermediate flushing fluid comprising a viscosity increasing agent.

8. The method of claim 1, further comprising flushing the medical device with a third flushing fluid after flushing the medical device with the second flushing fluid, wherein the third flushing fluid is saline or a second buffer solution.

9. The method of claim 1, wherein the first and/or second buffer solution comprises a buffering agent that is one or more selected from a group consisting of glycine, lysine, ammonium, borate, TRIS, HEPES, phosphate, histidine, and arginine.

10. The method of claim 1, wherein the second flushing fluid is pH-adjusted.

11. The method of claim 1, wherein the first and/or second buffer solution has a pH of 7 to 10.5.

12. The method of claim 1, wherein a concentration of the buffering agent in the first and/or second buffer solution is 0.01 molar to 1.0 molar.

13. The method of claim 1, wherein the second and/or third flushing fluid is saline.

14. The method of claim 1, wherein the second and/or third flushing fluid is an acidic buffer.

15. The method of claim 14, wherein the acidic buffer comprises phosphate or acetate.

16. The method of claim 11, wherein the first and/or second buffer solution has a pH of 8 to 10.

17. The method of claim 11, wherein the first and/or second buffer solution has a pH of 9.5 to 9.7.

18. The method of claim 11, wherein the first and/or second buffer solution has a pH of 9.6.

19. The method of claim 12, wherein the concentration of the buffering agent in the first and/or second buffer solution is 0.05 molar to 0.5 molar.

20. The method of claim 12, wherein the concentration of the buffering agent in the first and/or second buffer solution is 0.1 molar.

* * * * *